US006627614B1

(12) United States Patent
Rubinfeld

(10) Patent No.: US 6,627,614 B1
(45) Date of Patent: Sep. 30, 2003

(54) SEQUENTIAL THERAPY COMPRISING A 20 (S)-CAMPTOTHECIN AND AN ANTHRACYCLINE

(75) Inventor: Joseph Rubinfeld, Danville, CA (US)

(73) Assignee: Super Gen, Inc., Dublin, CA (US)

( * ) Notice: Subject to any disclaimer, the term of this patent is extended or adjusted under 35 U.S.C. 154(b) by 0 days.

(21) Appl. No.: 10/163,520

(22) Filed: Jun. 5, 2002

(51) Int. Cl.⁷ .............................................. A61K 31/70
(52) U.S. Cl. ........................... 514/34; 514/25; 514/283
(58) Field of Search ........................... 514/25, 34, 100, 514/283

(56) References Cited

U.S. PATENT DOCUMENTS

| 5,552,154 | A | * | 9/1996 | Giovanella et al. ......... 424/449 |
| 5,786,344 | A | * | 7/1998 | Ratain et al. ................ 514/100 |
| 6,403,563 | B1 | * | 6/2002 | Geroni et al. ................. 514/34 |
| 6,420,377 | B1 | * | 7/2002 | Lee et al. .................... 514/280 |
| 2002/0002162 | A1 | * | 1/2002 | Lee ............................. 514/221 |
| 2002/0123469 | A1 | * | 9/2002 | Brown ........................ 514/25 |

OTHER PUBLICATIONS

Pavillard et al, Br. J. Cancer, vol. 85(7), pp. 1077–1083 (abstract), Sep. 2001.*
Tolcher et al, Clin. Cancer Res., vol. 3(5), pp. 755–760 (abstract) May 1997.*
Eder et al. Cancer Chem. Pharm., vol. 42, pp. 327–335, 1998.*

* cited by examiner

Primary Examiner—James H Reamer
(74) Attorney, Agent, or Firm—Shirley Chen; Wilson Sonsini Goodrich & Rosati

(57) ABSTRACT

A method is provided for treating a patient having a disease associated with undesirable or uncontrolled cell proliferation. The method comprises: administering to the patient an anthracycline for a period of time during which a 20(S)-camptothecin is not present in a pharmacologically active form in patient's blood; and administering a 20(S)-camptothecin to the patient.

53 Claims, No Drawings

SEQUENTIAL THERAPY COMPRISING A 20 (S)-CAMPTOTHECIN AND AN ANTHRACYCLINE

BACKGROUND OF THE INVENTION

1. Field of the Invention

This invention relates to a method for treating disease using a 20(S)-camptothecin and an anthracycline, and more specifically a method for treating disease using a 20(S)-camptothecin and an anthracycline in a sequential therapy.

2. Description of Related Art

A. 20(S)-Camptothecins

20(S)-camptothecin, a plant alkaloid, was found to have anticancer activity in the late 1950's. Wall, M. et al., *Plant antitumor agents. I. The isolation and structure of camptothecin, a novel alkaloidal leukemia and tumor inhibitor from Camptotheca acuminata*, J. Am. Chem. Soc. 88: 3888–3890, (1966); Monroe E. Wall et al., *Camptothecin: Discovery to Clinic*, 803 Annals of the New York Academy of Sciences 1 (1996). These documents, and all documents articles, patents, etc.) cited to herein, are incorporated by reference into the specification as if reproduced fully below. The chemical formula of camptothecin was determined to be $C_{20}H_{16}N_2O_4$.

20(S)-camptothecin itself is insoluble in water. However, during the sixties and seventies the sodium salt of 20(S)-camptothecin was derived from 20(S)-camptothecin through opening of the lactone ring using a mild base. Clinical trials were then conducted using this hydrosoluble, sodium salt derivative of 20(S)-camptothecin 20(S)-camptothecin Na+), which was administered intravenously. The studies were later abandoned because of the high toxicity and low potency of 20(S)-camptothecin $Na^+$. Gottlieb, J. A., et al., *Preliminary pharmacological and clinical evaluation of camptothecin sodium salt (NSC 100880)*, Cancer Chemother. Rep. 54:461–470 (1979); Muggia, F. M., et al., *Phase I clinical trials of weekly and daily treatment with camptothecin (NSC 100880): Correlation with clinical studies*, Cancer Chemother. Rep. 56:515–521 (1972); Gottlieb, J. A. et al., *Treatment of malignant melanoma with camptothecin (NSC 100880)*, Cancer Chemother. Rep. 56:103–105 (1972); and Moertel, C. G., et al., *Phase II study of camptothecin (NSC 100880) in the treatment of advanced gastrointestinal cancer*, Cancer Chemother Rep. 56:95–101 (1972).

Despite its potential, interest in 20(S)-camptothecin as a therapeutic remained at a low ebb until the mid-1980's. By that time, drug therapies were being evaluated for treating human cancer using human cancer xenograft lines. During these evaluations, human tumors are serially heterotransplanted into immunodeficient, so-called Anude@ mice, and the mice then tested for their responsiveness to a specific drug (Giovanella, B. C., et al., Cancer 52(7): 1146 (1983)). The data obtained in these studies strongly support the validity of heterotransplanted human tumors into immunodeficient mammals, such as nude mice, as a predictive model for testing the effectiveness of anticancer agents.

20(S)-camptothecin, and later some of its substituted forms, elicited differential responses in the cell cycle of nontumorigenic and tumorigenic human cells in vitro. Although it is not yet understood why 20(S)-camptothecin and some of its substituted forms are cytostatic for nontumorigenic cells and cytotoxic for tumorigenic cells, the selective toxicity of the compounds against tumorigenic cells in vitro and in vivo was an especially interesting feature of these drugs.

Investigators began to experiment with various substituted forms of 20(S)-camptothecin. Good activity was found when various substitutions were made to the 20(S)-camptothecin scaffold. For example, (9-Amino-20(S)-Camptothecin (9AC) and 10,11-Methylendioxy-20(S)-Camptothecin (10,11 MD) are capable of having high anticancer activity against human colon cancer xenografts. Giovanella, B. C., et al., *Highly effective topoisomerase-1 targeted chemotherapy of human colon cancer in xenografts*, Science 246:1046–1048 (1989).

Additionally, 9-nitrocamptothecin (9NC) has shown high activity against human tumor xenograft models. 9NC has a nine position hydrogen substituted with a nitro moiety. 9NC has inhibited the growth of human tumor xenografts in immunodeficient nude mice and has induced regression of human tumors established as xenografts in nude mice with little or no appearance of any measurable toxicity. D. Chatterjee et al., *Induction of Apoptosis in Malignant and Camptothecin-resistant Human Cells*, 803 Annals of the New York Academy of Sciences 143 (1996).

U.S. Pat. No. 5,552,154 to Giovanella et al. disclosed methods of treating specific forms of cancer with water-insoluble 20(S)-camptothecin and derivatives thereof, having the closed-lactone ring intact. In particular, transdermal, oral and intramuscular methods of administration using solutions of water-insoluble 20(S)-camptothecin were disclosed.

Other substituted 20(S)-camptothecin compounds that have shown promise include 7-ethyl-10-hydroxy 20(S)-camptothecin, and other 7, 9, 10, 11-substituted compounds.

B. Anthracyclines

Anthracyclines are commonly known to be highly active antineoplastic agents. Anthracyclines include rhodomycin derivatives, including doxorubicin, duanorubicin, idarubicin, epirubicin, and mitoxantrone, as well as agents such as aclacinomycin A and related compounds.

Anthracyclines are known cytostatic agents, e.g., they inhibit or suppress cell growth and multiplication. Antracyclines act by an incompletely understood mechanism, which includes some antihelicase activity, and have been observed to exert a differentiation-inducing effect.

Anthracyclines, which comprise a four membered anthracycline nucleus attached to a sugar molecule, are clinically important anti-neoplastic agents. Doxorubicin is widely used in treating several solid tumors while daunorubicin and idarubicin are used exclusively for the treating leukemias. Daunorubicin and doxorubicin are identical except for the presence of a hydrogen or hydroxyl at position 14 of the anthracycline ring. Idarubicin, 4-demethoxy-daunorubicin, is a new anthracycline in which the structural modification at position 4 of the chromophore ring increases lipophilicity and half-life.

Anthracyclines bind double stranded DNA by intercalation as has been demonstrated experimentally. Their cytotoxicity largely results from this binding. Human chromosome preparations treated with anthracyclines exhibit the bound drug as defined, orange-red fluorescent bands. If structure of the anthracyclines is modified to reduce intercalative binding of DNA, a decrease or loss of antitumor activity is usually observed. Thus, DNA binding appears critical for anti-neoplastic activity of these drugs.

The specific mechanism of cytotoxicity is not clearly understood. Because inhibition only of DNA and RNA synthesis occurs at high drug concentration only, it is not thought critical to cytotoxicity. Anthracyclines exert a number of cellular physiologic effects, any one or a combination of which may mechanistically effect their cytotoxicity.

By intercalating DNA, anthracyclines can affect many functions of the DNA including DNA and RNA synthesis. Breakage of the DNA strand can also occur. This is believed to mediated either by inhibition of the enzyme DNA Topoisomerase II (hTopII) or by the formation of free radicals. Inhibition of the enzyme hTopII, for example, can lead to a series of reactions leading to double strand breaks in the DNA. Thus the mechanism of action of anthracyclines is complex and at best poorly understood.

As camptothecin inhibits human topoisomerase I (hTopI) which possesses multiple enzymatic activities. It influences the topology of DNA as does hTopII, which is evidenced to be inhibited by the anthracyclines. But hTopI is also capable of phosphorylating proteins essential for mRNA splicing, evidencing hTopI involvement in the RNA splicing process. Inhibitors of hTopI such as camptothecins are therefore important anti-neoplastic pharmacotherapeutic agents.

Because hTopI, a 765-amino-acid nuclear enzyme (Stewart et al. (1996) *J. Biol. Chem.* 271:7593–601) involved in topological changes of DNA structure (Pommier et al. 1998) *Biochim. Biophys. Acta* 1400:83–106), plays key roles in DNA replication, transcription, and recombination, collectively DNA metabolism. During the hTopI catalytic process, a transient covalent linkage, termed a 'cleavable complex', forms between hTopI and DNA strand nicks. Camptothecins specifically target hTopI, binding noncovalently to cleavable complexes, to stabilize them and inhibit religation (Fan et al. 1998) *J. Med. Chem.* 41:2216–26), promoting formation of single-and double-strand DNA breaks, resulting in premature termination of replication and inhibition of transcription (Bendixen et al. (1990) *Biochemistry* 29:5613–19). Cells can repair DNA breaks, permitting cell survival with exposure to low doses of camptothecins, but higher doses lead to cell death (Darzynkiewicz et al. 1996) *Ann. N. Y. Acad. Sci.* 803:90–100). Because many neoplastic cells exhibit high levels and/or activities of hTopI Giovanella et al. (1989) *Science* 246:1046–48; Husain et al. (1994) *Cancer Res.* 54: 539–46), hTopI has become a cellular target for anticancer chemotherapy O'Leary et al. (1998) *Eur. J. Cancer.* 34:1500–08; Takimoto et al. (1998) *Biochim. Biophys. Acta* 1400:107–119). Camptothecin derivatives such as topotecan and irinotecan (CPT-11) are currently used in the treatment of various cancers O'Leary et al. 1998) supra; Takimoto et al. (1998) supra; Beran et al, (1998) *Semin Oncol* 35:26–31). In patients who received high doses of hTopI inhibitors, only limited side effects, such as manageable neutropenia, have been reported O'Leary et al. (1998) supra; Takimoto et al. (1998) supra).

Although hTopI and hTopII are structurally diverse enzymes that generate transient single or double strand breaks in the DNA phosphodiester backbone to allow the passage of one or two DNA strands during replication by apparently different mechanisms, certain intercalating agents have been reported to inhibit both. This observation further complicates the current understanding of the mechanisms of action and inhibition of these two enzymes. Specifically, DNA-intercalating tricyclic carboxamides have the dual activity of both hTopI and hTopII inhibition Malonne et al. (1997) *Anti-Cancer Drugs* 8:811–22). The crystal structure of several such compounds with the DNA sequence CG(5BrU)ACG reveals a quadruplex-like intercalation cavity.

Thorpe et al. (2000) *Biochemistry* 39:15055–61 have previously shown that 9-aminoacridinecarboxamides hTopII inhibitors) can intercalate into duplex DNA, with the carboxamide side chain oriented by H-bonding to the cationic ring nitrogen of the acridine to lie in the major groove; thus oriented they specifically bind to adjacent guanines (Todd et al. (1999) *J. Med Chem.* 42:536–40). These observations, and consistent data obtained using purified topoisomerases in vitro to study drug-induced cleavable complex formation, suggest that the tricyclic carboxamides have different binding sites, altered sequence specificity or a different mechanism of action from other topoisomerase poisons. Thus the mechanisms of the hTopI and hTopII inhibitory activity of camptothecins and anthracyclines respectively are incompletely understood with respect to DNA physiology. Indeed the additionally evidenced effects of hTopI that do not involve DNA metabolism, evidence of the roles hTopII and hTopII play in cellular physiology in general, are poorly understood.

In U.S. Pat. No. 5,786,344 to Ratain et al., numerous genera of agents, including anthracyclines, are listed for possible combination with camptothecins. Bertrand et al. (1992) *Eur. J. Cancer*, 28A(4–5):743–48 observed an antagonism from simultaneous administration of the hTopI inhibitor and hTopII inhibitor. Various antineoplastic sequential therapies in which hTopI inhibitors, including camptothecins are found effective when administered prior to agents that are not hTopI inhibitors. See for example, Mori et al. (1993) *Int. J. Gynecol. Cancer*: 3(1):36–43.

SUMMARY OF THE INVENTION

A method is provided for treating a patient having a disease associated with undesirable or uncontrolled cell proliferation, the method comprising: administering to the patient an anthracycline for a period of time during which a 20(S)-camptothecin is not being administered to the patient; and administering a 20(S)-camptothecin to the patient.

According to this method, the anthracycline is optionally administered at least 10, 20, 30, 40, 50, or more days before the 20(S)-camptothecin is administered. Also according to this method, the anthracycline is optionally administered between 10 and 120 days, 20 and 120 days, 30 and 120 days, 40 and 120 days, or 50 and 120 days before the 20(S)-camptothecin is administered.

Also according to this method, the anthracycline is optionally administered at least 10, 20, 30, 40, 50, or more days after the 20(S)-camptothecin is administered. Also according to this method, the anthracycline is optionally administered between 10 and 120 days, 20 and 120 days, 30 and 120 days, 40 and 120 days, or 50 and 120 days after the 20(S)-camptothecin is administered.

Also according to this method, the anthracycline is optionally administered between 10 and 120 days, 20 and 120 days, 30 and 120 days, 40 and 120 days, or 50 and 120 before and/or after the 20(S)-camptothecin is administered and is also administered within that period of time when the 20(S)-camptothecin is administered.

A method is also provided for treating a patient having a disease associated with undesirable or uncontrolled cell proliferation, the method comprising: administering to the patient an anthracycline for a period of time during which a 20(S)-camptothecin is not present in a pharmacologically active form in the patient's body; and administering a 20(S)-camptothecin to the patient.

According to this method, the anthracycline is optionally administered at least 10, 20 30, 40, 50, or more days before the 20(S)-camptothecin is present in a pharmacologically active form in the patient's body. Also according to this method, the anthracycline is optionally administered between 10 and 120 days, 20 and 120 days, 30 and 120 days, 40 and 120 days, or 50 and 120 before the 20(S)-camptothecin is present in a pharmacologically active form in the patient's body.

Also according to this method, the anthracycline is optionally administered at least 10, 20, 30, 40, 50, or more days after the 20(S)-camptothecin is present in a pharmacologically active form in the patient's body. Also according to this method, the anthracycline is optionally administered between 10 and 120 days, 20 and 120 days, 30 and 120 days, 40 and 120 days, or 50 and 120 after the 20(S)-camptothecin is present in a pharmacologically active form in the patient's body.

Also according to this method, the anthracycline is optionally administered between 10 and 120 days, 20 and 120 days, 30 and 120 days, 40 and 120 days, or 50 and 120 before or after the 20(S)-camptothecin is present in a pharmacologically active form in the patient's body and is also administered when the 20(S)-camptothecin is present in a pharmacologically active form in the patient's body.

In regard to the methods of the present invention, in one variation, the anthracycline is selected from the group consisting of: doxorubicin, duanorubicin, idarubicin, epirubicin, and mitoxantrone and aclacinomycin A. In one particular variation, the anthracycline is doxorubicin.

In regard to the methods of the present invention, in one variation, the 20(S)-camptothecin is 9-nitro-20(S)-camptothecin.

In regard to the methods of the present invention, in one variation, the disease associated with undesirable or uncontrolled cell proliferation is cancer. Examples of cancers include, but are not limited to acute myelogenous leukemia, cholangiocarcinoma, chronic myelogenous leukemia, lymphoma, melanoma, multiple myeloma, osteosarcoma, gastric sarcoma, glioma, bladder, breast, cervical, colorectal, lung, ovarian, pancreatic, prostrate, and stomach cancer.

DETAILED DESCRIPTION OF THE INVENTION

The present invention relates to the sequential delivery of a 20(S)-camptothecin and an anthracycline where one therapeutic agent, most typically the anthracycline, is administered to a patient for a period of time during which the other therapeutic agent is not administered to the patient. Optionally, one therapeutic agent is administered to a patient when the other is not present in a pharmacologically active form in the patient's body, for example in the patient's blood stream. The period of time when only one of the therapeutic agents is administered or where only one of the therapeutic agents is present in a pharmaceutically active form in the patient's body may be at least ten, twenty, thirty, forty, fifty, or more days.

It is noted that sequential delivery optionally also includes periods of time where both therapeutic agents are administered to the patient and/or where both therapeutic agents are present in pharmaceutically active forms in the patient's body.

By administering these different therapeutic agents to a patient for periods of time where one but not the other therapeutic is administered, it is believed that these therapeutic agents will be more effective than if only one of the therapeutic agents is administered to the patient.

In some instances, diseased cells develop a tolerance for a given therapeutic agent over time. As a result, the efficacy of that therapeutic agent decreases. By sequentially administering a 20(S)-camptothecin such as 9-nitro-20(S)-camptothecin or an anthracycline such as doxorubicin, some diseased cells are killed while other diseased cells are weakened but develop a resistance to the therapeutic agent. Then, by switching between the 20(S)-camptothecin and the anthracycline after administering one of them for a period of time, it is believed that the other therapeutic agent is better able to kill off the remaining diseased cells that had been weakened by the therapeutic agent that was first administered.

In one particular embodiment, the sequential method is employed for treating pancreatic cancer.

In one embodiment, sequential therapy is performed according to the present invention where an anthracycline such as doxorubicin is administered at least a portion of time when a 20(S)-camptothecin such as 9-nitro-20(S)-camptothecin is not administered to the patient.

A portion of the time when the anthracycline is administered may optionally be when no pharmaceutically active a 20(S)-camptothecin such as 9-nitro-20(S)-camptothecin is present in the patient's body. It may be that an anthracycline is administered earlier than a pharmacologically active form of the 20(S)-camptothecin enters the patient's system. It also may be that an anthracycline is administered after the previously administrated a 20(S)-camptothecin is processed by the patient's system. It also may be that an anthracycline is administered when only pharmacologically or therapeutically inactive forms of a 20(S)-camptothecin are present in patient's body.

The anthracycline is optionally administered at least ten, twenty, thirty, forty, fifty, or more days before or after the administration of the 20(S)-camptothecin and/or the presence of the 20(S)-camptothecin in a pharmacologically active form in the patient's body.

In one variation, administration of an anthracycline includes administration before the 20(S)-camptothecin is administered. Administration of an anthracycline may also include administration after the 20(S)-camptothecin is administered. Optionally, an anthracycline is administered to the patient both before and after the 20(S)-camptothecin is administered. Optionally, an anthracycline is administered to the patient for a period of time before the 20(S)-camptothecin is administered, while the 20(S)-camptothecin is administered and for a period of time after the 20(S)-camptothecin is administered. It should be recognized that multiple cycles of administration may be performed where an anthracycline is administered and then a 20(S)-camptothecin is administered, or where an anthracycline is administered and the 20(S)-camptothecin is administered periodically administered during the time the anthracycline is administered.

In one variation, one or more repetitive cycles are performed comprising one or more doses of an anthracycline and one or more doses of a 20(S)-camptothecin. As noted, cycles of administration of an anthracycline and cycles of administration of 20(S)-camptothecin may overlap.

Optionally, an anthracycline is first administered to the patient until a physiological state is observed in the patient. Accordingly, the method may include administering the anthracycline and measuring one or more physiological states until a predetermined physiological state is reached, at which point administration of the anthracycline is discontinued. A 20(S)-camptothecin such as 9-nitro-20(S)-camptothecin may then be may be administered.

In regard to each of the above variations, the patient may optionally be taken off treatment with one agent for a period of time before receiving the other agent. For example, the period of time may be between one and sixty weeks, preferably between one and four weeks.

Optionally, the patient is treated sequentially with the anthracycline and the 20(S)-camptothecin in repeated iterations. More specifically, the patient may receive an anthracycline, then a 20(S)-camptothecin, then an anthracycline, etc.

Examples of particular physiological indicia for performing sequential treatment according to the present invention include, but are not limited to when the patient possesses one or more of the following: a point mutation in p53 in the tumor specimen were detected or, if p14 Arf might be expressed inappropriately or, if MDM-2 might be overexpressed above endogenous normal levels, or if MDM-2 showed aberrant phosphorylation levels due to hyperactive ras or growth factor pathways in the tumor.

One particular application of sequential treatments according to the present invention is their use in treating pancreatic cancer.

1. 20(S)-Camptothecin Compounds

As used herein, a 20(S)-camptothecin refers to any compound which comprises the general 20(S)-camptothecin scaffold. As such, 20(S)-camptothecin encompasses a wide range of substituted 20(S)-camptothecins including, 7, 9, 10, 11, 12-substituted compounds. Such substitutions may serve to provide differential activities over the unsubstituted camptothecin compound. Especially preferable are 9-nitrocamptothecin, 9-aminocamptothecin, 10,11-methylendioxy 20(S)-camptothecin, topotecan, irinotecan, 7-ethyl-10-hydroxy camptothecin, or another substituted camptothecin that is substituted at least one of the 7, 9, 10, 11, or 12 positions. Particular examples of substituted 20(S)-camptothecins include, but are not limited to, 9-nitro-20(S)-camptothecin, 9-amino-20(S)-camptothecin, 9-methyl-camptothecin, 9-chlorocamptothecin, 9-flouro-camptothecin, 7-ethyl camptothecin, 10-methylcamptothecin, 10-chloro-camptothecin, 10-bromo-camptothecin, 10fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10, 11-methylenedioxy camptothecin.

It should be recognized that these camptothecins may optionally be further substituted. In one particular variation, the 20(S)-camptothecin is 9-nitro-20(S)-camptothecin.

2. Anthracyclines

A variety of anthracyclines may be used in sequential therapy with a 20(S)-camptothecin, particularly 9-nitro-20(S)-camptothecin and 9-amino-20(S)-camptothecin. Anthracyclines generally refers to a class of compounds having the below ring structure including analogs and derivatives, pharmaceutical salts, esters, and conjugates thereof. It is noted that the below structure is that of doxorubicin.

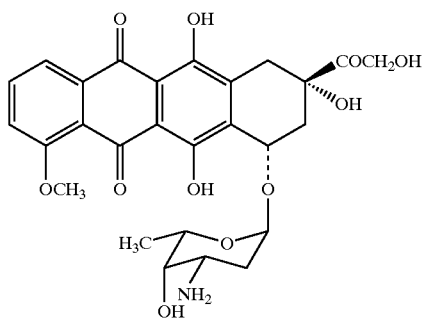

Examples of anthracyclines and anthracycline analogs include, but are not limited to, rhodomycin, daunorubicin (daunomycin), doxorubicin (adriamycin), epirubicin, pyrarubicin, idarubicin, 5-iminodaunomycin, mitoxantrone and aclacinomycin A (aclarubicin). Mitoxantrone is a member of the anthracendione class of compounds, which are anthracycline analogs that lack the sugar moiety of the anthracyclines but retain the planar polycylic aromatic ring structure that permits intercalation into DNA.

Specifically contemplated as anthracyclines in the context of the instant invention are all analogs and derivatives, including prodrugs and conjugates as well as scaffold substituted species of all anthracycline species enumerated herein and salts esters conjugates and stereoisomers thereof.

3. Indications for Sequential Therapy

Preferable indications that may be treated using the sequential therapies of the present invention include those involving undesirable or uncontrolled cell proliferation. Such indications include restenosis, benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Specific types of restenotic lesions that can be treated using the present invention include coronary, carotid, and cerebral lesions. Specific types of benign tumors that can be treated using the present invention include hemangiomas, acoustic neuromas, neurofibroma, trachomas and pyogenic granulomas. Specific types of cancers that can be treated using this invention include acute myelogenous leukemia, bladder, breast, cervical, cholangiocarcinoma, chronic myelogenous leukemia, colorectal, gastric sarcoma, glioma, leukemia, lung, lymphoma, melanoma, multiple myeloma, osteosarcoma, ovarian, pancreatic, prostrate, stomach, or tumors at localized sites including inoperable tumors or in tumors where localized treatment of tumors would be beneficial, and solid tumors. In a more preferable embodiment, the types of cancer include pancreatic, and/or colorectal.

Treatment of cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

Abnormal angiogenesis that may be may be treated using this invention include those abnormal angiogenesis accompanying rheumatoid arthritis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

4. Delivery and Dosing of Therapeutic Agents

A wide variety of delivery methods and formulations may be used to separately deliver the 20(S)-camptothecin and the anthracycline. For example, each agent may be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery for example by catheter or stent), subcutaneously, intraadiposally, intraarticularly, or intrathecally. The agents may optionally be administered in slow release dosage forms.

A variety of dosing regiments have been developed for 20(S)-camptothecins and anthracyclines, each depending on the particular indication and route of administration to be employed. Each therapeutic agent may be administered in any conventional dosage form.

Optionally, the following dosing ranges may be used per 50 kilogram body mass for a treatment or administration cycle of either a 20(S)-camptothecin: 10 to 4000 mg of the agent; 100 to 2000 mg; 200 to 1500 mg; or 500 to 1100 mg.

Provided herein are exemplary dosing schemes for different indications. It should be understood, however, that other dosing schemes may be employed without departing from the present invention.

A. 9-Nitro-20(S)-Camptothecin

In one variation, 9-nitro-20(S)-camptothecin is administered orally. The dosing range suggested for this route of administration is typically between 0.3 mg/m$^2$/day/patient (minimum) and 3 mg/m$^2$/day/patient (maximum). For example, a preferred dose for patients with pancreatic cancer is 1.5 mg/m$^2$/day/patient. It is recommended to adjust the dose of 9-nitro-20(S)-camptothecin according to the patient's needs, preferring a higher dose when the overall response to the drug is positive, or preferring a lower dose when toxicity or progression of the disease is a problem.

9-Nitro-20(S)-camptothecin may be administered orally for two, three, four or five consecutive days followed by one or several days of rest. This cycle may be repeated for two or more weeks. For example, for patients with pancreatic cancer, a 7-day schedule is preferred where 5 consecutive days of administration are followed by 2 days of rest. Because of the toxicity, the described cycle can be modified to shorten the number of days when 9-nitro-20(S)-camptothecin is administered. In some instances, it may be desirable to periodically discontinue 9-nitro-20(S)-camptothecin for one or more days, after which, administration is repeated.

In one example, a 8-week cycle of 9-nitro-20(S)-camptothecin administration is performed. If toxicity or progression of the disease is a major concern, the treatment can be discontinued at any time. If the patient demonstrates a positive response to the drug, the treatment may be prolonged for 90-weeks or longer.

In one particular example, patients with various types of cancer, including primary cancer and metastasis, receive orally 9-Nitro-20(S)-camptothecin. The dosage ranges between 1 and 2.5 mg/m$^2$/day for 5 consecutive days followed by 2 days of rest. Dose escalations are permitted. Dose reductions are permitted when necessary and range as low as 0.6 mg/m$^2$/day 5 days on, 2 days off). Patients are treated for as long as the overall response to the treatment is positive. The median number of weeks per patient is 11 (range 1 to 83 weeks). The dose limiting toxicity is hematological and gastrointestinal. The group of tumors that are known to regress after exposure to 9-Nitro-20(S)-camptothecin comprises of breast carcinoma, ovarian carcinoma, cholangiocarcinoma, monomyelocytic leukemia, and pancreatic carcinoma.

B. Doxorubicin

A variety of different formulations and delivery motifs have been developed for doxorubicin. For example, doxorubicin may be administered intravenously, for example at a dose of 20 mg/m$^2$, twice per week.

Doxorubicin may also be administered in conjunction with liposomes. Liposomes are microscopic globules of fat, that change pharmokinetics of doxorubicin, thus achieving a different targeting of the therapy.

Doxorubicin may also be administered as a pegylated liposomal hydroclorate of doxorubicin, marketed by Schering-Plough Inc. Kenilworth, N.J., under the name Caelyx®. In this form, doxorubicin is typically administered according to manufacturer's protocol. Briefly, Caelyx® is recommended to be administered intravenously at a dose of 50 mg/m$^2$ once every four weeks for as long as the disease does not progress and the patient continues to tolerate treatment.

A liposomal form of doxorubicin developed by Sequus Pharmaceuticals Inc., Menlo Park, Calif., and marketed by Alza Inc., Mountain View, Calif. under the name Doxil® may also be administrated according to manufacturer's protocol. Doxil® should be given only by intravenous infusion. The preferred cumulative dose of Doxil® is 120 mg/m$^2$, preferred maximum is 450 mg/m$^2$. Dox-SL®—a commercial variation of Doxil®—is administered analogously.

Doxorubicin is also available in a liposomal form marketed by Pharmacia Inc., Milan, Italy, under the name Adriamycin® and may be administrated according to manufacturer's protocol. Adriamycin RDF® (Doxorubicin Hydrochloride for Injection, USP) is a sterile red-orange lyophilized powder for intravenous use only. It is available in 10, 20 and 50 mg single dose vials and a 150 mg multidose vial. Each 10 mg single dose vial contains 10 mg of doxorubicin HCl, USP, 50 mg of lactose, NF (hydrous) and 1 mg of methylparaben, NF (added to enhance dissolution) as a sterile red-orange lyophilized powder. Each 20 mg single dose vial contains 20 mg of doxorubicin HCl, USP, 100 mg of lactose, NF (hydrous) and 2 mg of methylparaben, NF (added to enhance dissolution) as a sterile red-orange lyophilized powder. Each 50 mg single dose vial contains 50 mg of doxorubicin HCl, USP, 250 mg of lactose, NF (hydrous) and 5 mg of methylparaben, NF (added to enhance dissolution) as a sterile red-orange lyophilized powder. Each 150 mg multidose vial contains 150 mg of doxorubicin HCl, USP, 750 mg of lactose, NF (hydrous) and 15 mg of methylparaben, NF (added to enhance dissolution) as a sterile red-orange lyophilized powder. Adriamycin PFS® (Doxorubicin Hydrochloride Injection, USP) is a sterile parenteral, isotonic solution for intravenous use only, containing no preservative, available in 5 mL (10 mg), 10 mL (20 mg), 25 mL (50 mg), and 37.5 mL (75 mg) single dose vials and a 100 mL (200 mg) multidose vial. Each mL contains doxorubicin HCl 2 mg, USP and the following inactive ingredients: sodium chloride 0.9% and water for injection q.s. Hydrochloric acid is used to adjust the pH to a target pH of 3.0. The most commonly used dose schedule when used as a single agent is 60 to 75 mg/m$^2$ as a single intravenous injection administered at 21-day intervals. The lower dosage should be given to patients with inadequate marrow reserves due to old age, or prior therapy, or neoplastic marrow infiltration.

Pharmacokinetic studies, determined in patients with various types of tumors undergoing either single or multi-agent therapy have shown that doxorubicin follows a multiphasic disposition after intravenous injection. The initial distributive half-life of approximately 5.0 minutes suggests rapid tissue uptake of doxorubicin, while its slow elimination from tissues is reflected by a terminal half-life of 20 to 48 hours. Steady-state distribution volumes exceed 20 to 30 L/kg and are indicative of extensive drug uptake into tissues. Plasma clearance is in the range of 8 to 20 mL/min/kg and is predominately by metabolism and biliary excretion. Approximately 40% of the dose appears in the bile in 5 days, while only 5 to 12% of the drug and its metabolites appear in the urine during the same time period. Systemic clearance of doxorubicin is significantly reduced in obese women with ideal body weight greater than 130%. There was a significant reduction in clearance without any change in volume of distribution in obese patients when compared with normal patients with less than 115% ideal body weight. The clearance of doxorubicin and doxorubicinol was also reduced in patients with impaired hepatic function. Doxorubicin does not cross the blood brain barrier.

It is recommended to adjust the dose of doxorubicin according to the patients needs, preferring a higher dose when the overall response to the drug is positive, or preferring a lower dose when toxicity or progression of the disease is a problem. The most serious danger of ordinary doxorubicin chemotherapy is toxicity to the heart, which occurs when a large cumulative dose is used. The irreversible cardiac toxicity may occur when the total cumulative dose approaches 550 mg/M$^2$, or less if patients have had other systemic chemotherapy, or have additional risk factors. Physicians advised to use special monitoring if they treat beyond this level. Doxorubicin may cause additional toxicity that are manifested by neutropenia, thrombocytopenia, anemia, confusion and hematuria.

The risk of congestive heart failure and other acute manifestations of doxorubicin cardiotoxicity in children may be as much or lower than in adults. Children appear to be at particular risk for developing delayed cardiac toxicity in that doxorubicin induced cardiomyopathy impairs myocardial growth as children mature, subsequently leading to possible development of congestive heart failure during early adulthood. As many as 40% of children may have subclinical cardiac dysfunction and 5 to 10% of children may develop congestive heart failure on long term follow-up. This late cardiac toxicity may be related to the dose of doxorubicin. The longer the length of follow-up the greater the increase in the detection rate. Treatment of doxorubicin induced congestive heart failure includes the use of digitalis, diuretics, after load reducers such as angiotensin I converting enzyme (ACE) inhibitors, low salt diet, and bed rest. Such intervention may relieve symptoms and improve the functional status of the patient.

Acute overdosage with doxorubicin enhances the toxic effect of mucositis, leukopenia and thrombocytopenia. Treatment of acute overdosage consists of treatment of the severely myelosuppressed patient with hospitalization, antimicrobials, platelet transfusions and symptomatic treatment of mucositis. Use of hemopoietic growth factor (G-CSF, GM-CSF) may be considered.

C. Exemplary Sequential Therapy Treatment Protocols

In this example, different protocols are described for administering 9-nitro-20(S)-camptothecin and doxorubicin to patients with primary or metastatic carcinoma of the pancreas.

Protocol 1.

According to this protocol, doxorubicin is first administered for a period of time, then 9-nitro-20(S)-camptothecin is administered. The Adriamycin RDF® formulation of doxorubicin is employed although it should be understood that other formulations of doxorubicin may also be substituted.

Adriamycin RDF® 10 mg, 20 mg, 50 mg, and 150 mg vials should be reconstituted with 5 mL, 10 mL, 25 mL, and 75 mL, respectively, of Sodium Chloride to give a final concentration of 2 mg/mL of doxorubicin hydrochloride. After adding the diluent, the vial should be shaken and the contents allowed to dissolve. The reconstituted solution is stable for 7 days at room temperature and 15 days under refrigeration 2° to 8° C.). It should be protected from exposure to sunlight.

When used in combination with 9-nitro-20(S)-camptothecin, doxorubicin is preferably given as a 40 to 60 mg/m$^2$ given as a single intravenous injection every 21 to 28 days. The number of cycles may vary between 1 and 10; the preferred number of cycles is 5.

Doxorubicin dosage must be reduced in case of hyperbilirubinemia as follows:

| Plasma bilirubin concentration (mg/dL) | Dosage reduction (%) |
|---|---|
| 1.2–3.0 | 50 |
| 3.1–5.0 | 75 |

It is recommended that Adriamycin PFS® be slowly administered into the tubing of a freely running intravenous infusion of Sodium Chloride Injection, USP, or 5% Dextrose Injection, USP. The tubing should be attached to a Butterfly® needle inserted preferably into a large vein. If possible, avoid veins overjoints or in extremities with compromised venous or lymphatic drainage. The rate of administration is dependent on the size of the vein, and the dosage. However, the dose should be administered in not less than 3 to 5 minutes. Local erythematous streaking along the vein as well as facial flushing may be indicative of too rapid an administration. A burning or stinging sensation may be indicative of perivenous infiltration and the infusion should be immediately terminated and restarted in another vein. On intravenous administration of doxorubicin, extravasation may occur with or without an accompanying burning or stinging sensation, even if blood returns well on aspiration of the infusion needle. If any signs or symptoms of extravasation have occurred, the injection or infusion should be immediately terminated and restarted in another vein. If extravasation is suspected, intermittent application of ice to the site for 15 min. q.i.d.×3 days may be useful.

Skin reactions associated with doxorubicin have been reported. Skin accidentally exposed to doxorubicin should be rinsed copiously with soap and warm water, and if the eyes are involved, standard irrigation techniques should be used immediately. The use of goggles, gloves, and protective gowns is recommended during preparation and administration of the drug.

Patients that demonstrate objective or symptomatic progression of pancreatic cancer after the competition of treatment with doxorubicin receive 9-nitro-20(S)-camptothecin. The sequential stage begins at least 21 days after patients have received their final dose of doxorubicin. The preferred dosage for oral administration of 9-nitro-20(S)-camptothecin is 1.5 mg/m$^2$/day. It is applied for 5 consecutive days followed by 2 days of rest. Dose escalations are permitted and range as high as 2 mg/m$^2$/day. The dose limiting toxicity is hematological and gastrointestinal. Dose reductions may be necessary to control toxicity and involve either reduction of dosage up to 0.6 mg/m$^2$/day), or keeping the same dose level and shortening the schedule to four days of treatment per week, or shortening the overall course of 9-nitro-20(S)-camptothecin administration. Patients are treated with 9-nitro-20(S)-camptothecin for as long as the overall response to the treatment is positive. The preferred number of weeks is 11 with a typical range being between 1 to 83 weeks.

Protocol 2.

According to this protocol, 9-nitro-20(S)-camptothecin is first administered for a period of time, then doxorubicin is administered. The Adriamycin RDF® formulation of doxorubicin is employed although it should be understood that other formulations of doxorubicin may also be substituted.

Patients initially orally receive 9-nitro-20(S)-camptothecin. The preferred dosage is 1.5 mg/m$^2$/day applied for 5 consecutive days followed by 2 days of rest. Dose adjustments are permitted and range between 0.5 and 2 mg/m$^2$/day. Patients are treated with 9-nitro-20(S)-camptothecin for as long as the overall response to the treatment is positive. The preferred number of weeks is 11 with a typical range being between 1 to 83 weeks.

Patients that demonstrate objective or symptomatic progressions of pancreatic cancer receive additional treatment with doxorubicin administered in a commercially available form named Adriamycin RDF®. The sequential stage begins at least 28 days after patients have received their final dose of 9-nitro-20(S)-camptothecin. Guidance for how to administer Adriamycin RDF® is provided in Protocol 1 and in the literature.

When used in combination with 9-nitro-20(S)-camptothecin, doxorubicin is preferably given as a 40 to 60 mg/m$^2$ given as a single intravenous injection every 21 to 28 days. The number of cycles may vary between 1 and 10; the preferred number of cycles is 5.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method for treating a patient having a disease associated with undesirable or uncontrolled cell proliferation, the method comprising:
   administering to the patient an anthracycline for a period of time during which a water insoluble 20(S)-camptothecin is not being administered to the patient; and
   administering the water insoluble 20(S)-camptothecin to the patient.

2. A method according to claim 1 wherein the anthracycline is administered at least 10 day before the 20(S)-camptothecin is administered.

3. A method according to claim 1 wherein the anthracycline is administered at least 20 days before the 20(S)-camptothecin is administered.

4. A method according to claim 1 wherein the anthracycline is administered at least 30 days before the 20(S)-camptothecin is administered.

5. A method according to claim 1 wherein the anthracycline is administered at least 40 days before the 20(S)-camptothecin is administered.

6. A method according to claim 1 wherein the anthracycline is administered at least 50 days before the 20(S)-camptothecin is administered.

7. A method according to claim 1 wherein the anthracycline is administered between 10 and 120 days before the 20(S)-camptothecin is administered.

8. A method according to claim 1 wherein the anthracycline is administered between 20 and 120 days before the 20(S)-camptothecin is administered.

9. A method according to claim 1 wherein the anthracycline is administered between 30 and 120 days before the 20(S)-camptothecin is administered.

10. A method according to claim 1 wherein the anthracycline is administered between 40 and 120 days before the 20(S)-camptothecin is administered.

11. A method according to claim 1 wherein the anthracycline is administered between 50 and 120 days before the 20(S)-camptothecin is administered.

12. A method according to claim 1 wherein the anthracycline is administered at least 10 day after the 20(S)-camptothecin is administered.

13. A method according to claim 1 wherein the anthracycline is administered at least 20 days after the 20(S)-camptothecin is administered.

14. A method according to claim 1 wherein the anthracycline is administered at least 30 days after the 20(S)-camptothecin is administered.

15. A method according to claim 1 wherein the anthracycline is administered at least 40 days after the 20(S)-camptothecin is administered.

16. A method according to claim 1 wherein the anthracycline is administered at least 50 days after the 20(S)-camptothecin is administered.

17. A method according to claim 1 wherein the anthracycline is administered between 10 and 120 days before or after the 20(S)-camptothecin is administered and is also administered within 10 days of when the 20(S)-camptothecin is administered.

18. A method according to claim 1 wherein the anthracycline is administered between 20 and 120 days before or after the 20(S)-caamptothecin is administered and is also administered within 20 days of when the 20(S)-camptothecin is administered.

19. A method according to claim 1 wherein the anthracycline is administered between 30 and 120 days before or after the 20(S)-camptothecin is administered and is also administered within 30 days of when the 20(S)-camptothecin is administered.

20. A method according to claim 1 wherein the anthracycline is administered between 40 and 120 days before or after the 20(S)-camptothecin is administered and is also administered within 40 days of when the 20(S)-camptothecin is administered.

21. A method according to claim 1 wherein the anthracycline is selected from the group consisting of: doxorubicin, duanorubicin, idarubicin, epirubicin, and mitoxantrone and aclacinomycin A.

22. A method according to claim 1 wherein the anthracycline is doxorubicin.

23. A method according to claim 1 wherein the 20(S)-camptothecin is 9-nitro-20(S)-camptothecin.

24. A method according to claim 1 wherein the disease associated with undesirable or uncontrolled cell proliferation is cancer.

25. A method according to claim 1 wherein the cancer is selected from the group consisting of acute myelogenous leukemia, cholangiocarcinoma, chronic myelogenous leukemia, lymphoma, melanoma, multiple myeloma, osteosarcoma, gastric sarcoma, glioma, bladder, breast, cervical, colorectal, lung, ovarian, pancreatic, prostrate, and stomach cancer.

26. A method according to claim 1 wherein the disease associated with undesirable or uncontrolled cell proliferation is pancreatic cancer.

27. A method for treating a patient having a disease associated with undesirable or uncontrolled cell proliferation, the method comprising: administering to the patient an anthracycline for a period of time during which a 20(S)-camptothecin is not present in a pharmacologically active form in patient's blood, and administering a 20(S)-camptothecin to the patient.

28. A method according to claim 27 wherein the anthracycline is administered at least 10 days before the 20(S)-camptothecin is present in a pharmacologically active form in patient's body.

29. A method according to claim 27 wherein the anthracycline is administered at least 20 days before the 20(S)-camptothecin is present in a pharmacologically active form in patient's body.

30. A method according to claim 27 wherein the anthracycline is administered at least 30 days before the 20(S)-camptothecin is present in a pharmacologically active form in patient's body.

31. A method according to claim 27 wherein the anthracycline is administered at least 40 days before the 20(S)-camptothecin is present in a pharmacologically active form in patient's body.

32. A method according to claim 27 wherein the anthracycline is administered at least 50 days before the 20(S)-camptothecin is present in a pharmacologically active form in patient's body.

33. A method according to claim 27 wherein the anthracycline is administered between 10 and 120 days before the 20(S)-camptothecin is present in a pharmacologically active form in patient's body.

34. A method according to claim 27 wherein the anthracycline is administered between 20 and 120 days before the 20(S)-camptothecin is present in a pharmacologically active form in patient's body.

35. A method according to claim 27 wherein the anthracycline is administered between 30 and 120 days before the 20(S)-camptothecin is present in a pharmacologically active form in patient's body.

36. A method according to claim 27 wherein the anthracycline is administered between 40 and 120 days before the 20(S)-camptothecin is present in a pharmacologically active form in patient's body.

37. A method according to claim 27 wherein the anthracycline is administered between 50 and 120 days before the 20(S)-camptothecin is present in a pharmacologically active form in patient's body.

38. A method according to claim 27 wherein the anthracycline is administered at least 10 day after the 20(S)-camptothecin is no longer present in a pharmacologically active form in patient's body.

39. A method according to claim 27 wherein the anthracycline is administered at least 20 days after the 20(S)-camptothecin is no longer present in a pharmacologically active form in patient's body.

40. A method according to claim 27 wherein the anthracycline is administered at least 30 days after the 20(S)-camptothecin is no longer present in a pharmacologically active form in patient's body.

41. A method according to claim 27 wherein the anthracycline is administered at least 40 days after the 20(S)-camptothecin is no longer present in a pharmacologically active form in patient's body.

42. A method according to claim 27 wherein the anthracycline is administered at least 50 days after the 20(S)-camptothecin is no longer present in a pharmacologically active form in patient's body.

43. A method according to claim 27 wherein the anthracycline is administered between 10 and 120 days before or after the 20(S)-camptothecin is present in a pharmacologically active form in patient's body and is also administered within 10 days of when the 20(S)-camptothecin is present in a pharmacologically active form in patient's body.

44. A method according to claim 27 wherein the anthracycline is administered between 20 and 120 days before or after the 20(S)-camptothecin is present in a pharmacologically active form in patient's body and is also administered within 20 days of when the 20(S)-camptothecin is present in a pharmacologically active form in patient's body.

45. A method according to claim 27 wherein the anthracycline is administered between 30 and 120 days before or after the 20(S)-camptothecin is present in a pharmacologically active form in patient's body and is also administered within 30 days of when the 20(S)-camptothecin is present in a pharmacologically active form in patient's body.

46. A method according to claim 27 wherein the anthracycline is administered between 40 and 120 days before or after the 20(S)-camptothecin is present in a pharmacologically active form in patient's body and is also administered within 40 days of when the 20(S)-camptothecin is present in a pharmacologically active form in patient's body.

47. A method according to claim 27 wherein the anthracycline is administered between 50 and 120 days before or after the 20(S)-camptothecin is present in a pharmacologically active form in patient's body and is also administered within 50 days of when the 20(S)-camptothecin is present in a pharmacologically active form in patient's body.

48. A method according to claim 27 wherein the anthracycline is selected from the group consisting of: doxorubicin, duanorubicin, idarubicin, epirubicin, and mitoxantrone and aclacinomycin A.

49. A method according to claim 27 wherein the anthracycline is doxorubicin.

50. A method according to claim 27 wherein the 20(S)-camptothecin is 9-nitro-20(S)-camptothecin.

51. A method according to claim 27 wherein the disease associated with undesirable or uncontrolled cell proliferation is cancer.

52. A method according to claim 27 wherein the cancer is selected from the group consisting of acute myelogenous leukemia, cholangiocarcinoma, chronic myelogenous leukemia, lymphoma, melanoma, multiple myeloma, osteosarcoma, gastric sarcoma, glioma, bladder, breast, cervical, colorectal, lung, ovarian, pancreatic, prostrate, and stomach cancer.

53. A method according to claim 27 wherein the disease associated with undesirable or uncontrolled cell proliferation is pancreatic cancer.

* * * * *